United States Patent

Krauleidies

Patent Number: 5,272,467
Date of Patent: Dec. 21, 1993

[54] APPARATUS FOR DETECTING AND REPORTING LIQUIDS

[76] Inventor: Horst Krauleidies, Possmoorweg 23, 2000 Hamburg 60, Fed. Rep. of Germany

[21] Appl. No.: 769,090

[22] Filed: Sep. 30, 1991

[30] Foreign Application Priority Data

Oct. 5, 1990 [DE] Fed. Rep. of Germany ....... 4031522

[51] Int. Cl.$^5$ ............................................. G08B 21/00
[52] U.S. Cl. .................................. 340/604; 340/619
[58] Field of Search ..................... 340/604, 605, 619

[56] References Cited

U.S. PATENT DOCUMENTS

| H652 | 7/1989 | Davis et al. | 340/605 |
| 4,789,853 | 12/1988 | Gentiluomo | 340/604 |
| 4,882,499 | 11/1989 | Luukkala et al. | 340/605 |
| 5,091,715 | 2/1992 | Murphy | 340/604 |

*Primary Examiner*—Glen R. Swann, III
*Attorney, Agent, or Firm*—Robert W. Becker & Associates

[57] ABSTRACT

An apparatus for detecting and reporting the presence of liquid on a surface has a detector unit that rests on the surface with the detector unit including at least one pair of spaced-apart electrodes for conductively detecting the liquid, with the detector unit resting on the surface via the electrodes, and with the detector unit further including a sensor that is directed toward the surface and serves for optically detecting the liquid. The apparatus also comprises an operations unit, with the detector unit and the operations unit being electrically interconnected.

9 Claims, 2 Drawing Sheets

APPARATUS FOR DETECTING AND REPORTING LIQUIDS

BACKGROUND OF THE INVENTION

The present invention relates to an apparatus for detecting and reporting or signalling the presence of liquid on a surface, and includes a detector unit that rests on the surface and an operations unit, with the detector unit and the operations unit being electrically interconnected.

Not only in the industrial arena, such as manufacturing plants, workshops, warehouses, offices, studios, and public facilities, but also in the private arena, such as in the household, enormous damage can result from discharging or leaking liquids, such as water, heating unit fluids, various hydrocarbons such as Diesel oil and gasoline, if the presence of these or any other liquids is not detected early enough. A number of attempts, some technically extremely complicated, have been undertaken to provide apparatus for systems that are in a position to detect and subsequently trigger an alarm concerning the presence of liquids that collect on an essentially flat base, for example on floors, as a result, for example, of a defect in a conveying line. Although it is still relatively easy to realize means for detecting a liquid such as water that, at least if it originates from a heating system, has a relatively good electrical conductivity, it has up now been extremely difficult, and actually without success, to provide detection means that with the same sensitivity are in a position to detect water originating from a heating system, water originating from a drinking water supply, as well as water originating from an air conditioning unit. A common detection of water originating from the aforementioned different sources is so extremely difficult for the reason that the electrical conductivity of water originating from a heating circuit is good, while the conductivity of water originating from a drinking water supply system is weak and water originating from an air conditioning unit has absolutely no electrical conductivity because such water must, by design, be demineralized. Up to now, in order in conformity with the very different conductivities of the various types of water, in each case separate apparatus had to be provided to be able to resolve such a problem at all.

As indicated above, the problems are, however, not exhausted by the detection of the various "water" liquids; rather, other liquids such as Diesel oil, volatile solvents, resins, cleaning fluids liquids used for cooling purposes. etc., cause much greater problems with regard to their detection when they are discharged or collect on a surface, such as the floor of a workshop or a warehouse, because such liquids generally have absolutely no electrical conductivity, and conductive agents for detecting these liquids are completely impossible to use, in contrast to the situation with aqueous solutions and water. Attempts have been made to detect such liquids in a capacitative manner, and to utilize the physical property of the differing magnitude of the dielectric constants $\Sigma_r$, whereby, for example, oil has a dielectric constant of $\Sigma_r = 2$ to 3, while water has a dielectric constant of $\Sigma_r = 81$. Thus, if a liquid level is to be detected pursuant to the capacitative method, it is roughly estimated that water would already have to have a level of 2 mm to be detected, while oil, due to its very small dielectric constant relative to water, could not be detected until a level of about 10 mm has been reached. Thus, the approach of determining the liquid level in a capacitative manner cannot be carried out without extreme capital outlay and measuring effort for liquids having varying dielectric constants.

Finally, a further serious problem that is encountered in conjunction with detecting various types of liquid that can collect on a surface is that the surface may not comprise a smooth metal, plastic, or concrete, but rather might be a textile floor covering, as is found not only in private rooms but also very often in commercial spaces. This problem is manifested, for example, where there is merely a defect in the water heating system or in water pipes, so that in contrast to a smooth floor or other surface, generally initially only a small area of the textile floor covering becomes soaked, and often this spot is covered by furniture or other devices and hence is not noticed. Thus, water or some other liquid can leak out unnoticed for a long period of time, resulting in serious damage. In addition, the structure of the textile floor covering, for example carpet pile secured to a base, can absorb considerable quantities of liquid and can prevent the same from flowing off, even if the floor or surface has a slight incline.

It is therefore an object of the present invention to provide an apparatus of the aforementioned general type that is suitable for detecting, with great precision, a large number of different liquids, that in addition is in a position to detect various types of liquid that accumulate not only on an unstructured, smooth surface, but also on structured surfaces and even on textile floor coverings, that is very straightforward in construction and requires no skilled artisan for assembly and installation, that is very easy and economical to produce and hence can be employed in large quantities, and that contributes to increasing the general safety.

BRIEF DESCRIPTION OF THE DRAWINGS

This object, and other objects and advantages of the present invention, will appear more clearly from the following specification in conjunction with the accompanying schematic drawing, in which.

SUMMARY OF THE INVENTION

Figure 1:
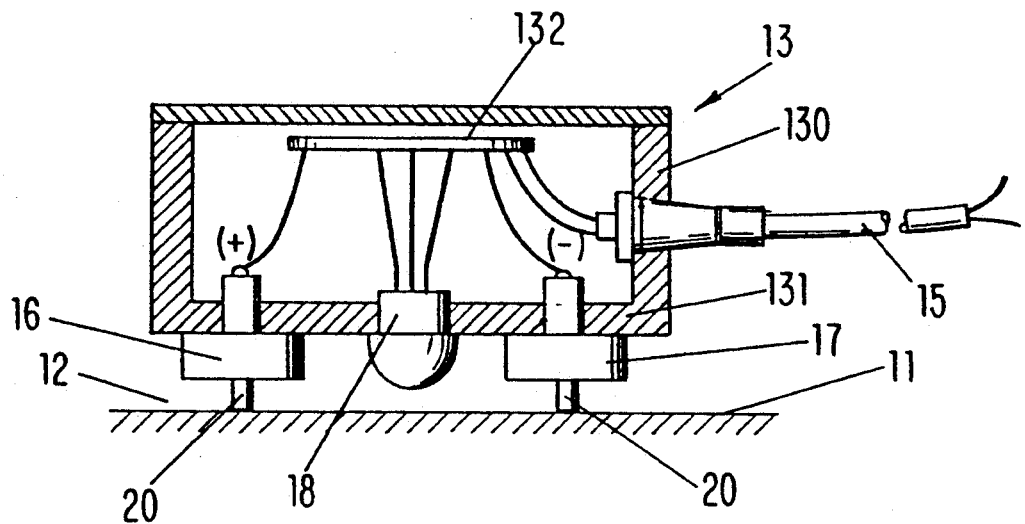
FIG. 1 is a cross-sectional side view of the detector unit of one exemplary embodiment of the inventive apparatus, with the detector unit resting upon a solid surface, such as the floor of a workshop.

The apparatus of the present invention is characterized primarily by: a detector unit that rests on the surface, with the detector unit including at least one pair of spaced-apart electrodes for conductively detecting the liquid, with the detector unit resting on the surface via the electrodes, and with the detector unit further including a sensor means that is directed toward the surface and serves for optically detecting the liquid; and an operations unit, with the detector unit and the operations unit being electrically interconnected.

The advantage of the inventive apparatus is essentially that due to the combination of the electrodes, which operate pursuant to the conductive principle, in a straightforward manner the stream that flows between the electrodes, for example if a conductive liquid is discharged, can be evaluated as an alarm signal, so that even very thin liquid films of less than 0.1 mm thickness can be detected. With the inventive sensor means, it is possible pursuant to the optical principle to detect all types of liquids at liquid levels of less than 2.5 mm thickness. Such sensor means utilizes the principle of light refraction at the boundary or contact surface of solid materials, whereby a sensor that is moistened with liquid has a different light refraction than does a non-moistened sensor. Not only the electrodes of the apparatus but also the sensor means operate continuously and in coordination with one another to detect different types of liquid with liquids that have conductive properties, such as heating system water, being detected in the apparatus by both of the detection systems (electrodes, sensor means).

Pursuant to one advantageous specific embodiment of the present invention, the electrodes have a laminar delimitation, i.e. have a surface, that extends essentially parallel to the surface upon which the apparatus rests, where preferably a pin-like projection is provided that extends from this surface. The purpose of this projection is to even further reduce the response level of the apparatus for non-conductive liquids. For example, if an apparatus equipped in this manner is positioned upon a textile floor covering, the projection easily extends into the textile structure, for example the pile of a carpet, to such a depth that the laminar surface portion of the electrode reliably comes to rest upon the upper surface of the textile floor covering.

Pursuant to a further advantageous specific embodiment of the inventive apparatus, the projection is integrally embodied with the electrode; in other words, for economical reasons the electrode can in principle be manufactured as a one-piece turned part.

The length of the projection can advantageously be adjusted differently, i.e. on the one hand advantageously different electrodes with different length projections can be provided that are connected with the detector unit in a suitable manner, for example by being pressed or screwed in; however, on the other hand it could also be advantageous to connect the projection with the electrode via a detachable mechanical connection, i.e. to standardize the electrode and to detachably connect to the rest of the electrode projections of various lengths via a plug connection, a screw connection, or any other type of connection.

In principle, it is advantageous to measure the length of the pin-like projection in such a way that when the apparatus rests upon a solid surface, at least the optically active surface of the sensor means does not contact the surface. Among other things, this provides a certain mechanical protection for the sensor means.

The detector unit, which preferably comprises a case-like housing having, for example, a circular cross-sectional configuration, can be provided with a plurality of electrode pairs that are disposed on the underside of the housing, i.e. on that surface of the housing that is adjacent to the surface upon which the apparatus is positioned. Independent of the number of electrode pairs, it is advantageous that at least the optically active surface of the sensor means be disposed between the electrodes of the electrode pair or pairs, as a consequence of which, among other things, a certain mechanical protection of the sensitive sensor surface is achieved, and external light is prevented from striking the sensor.

The electronic evaluation circuitry of the inventive apparatus is provided in conformity with generally known electronic principles; however, it is designed in such a way that advantageously the electrical current consumption of the detector unit when liquid is detected is the measurement parameter for an electrical and/or audible signal of the apparatus. To utilize the electrical current consumption as the measurement parameter has the considerable advantage that an electrical connection between the detector unit and the operations unit can comprise a two-wire connection, which can be easily placed and possibly also easily lengthened. Furthermore, this type of measurement parameter has the advantage that such defects or failures as an interruption of this line connection, or also a short circuit in the detector unit, can also be detected and reported.

Further specific features of the present invention will be described in detail subsequently.

DESCRIPTION OF PREFERRED EMBODIMENTS

Figure 3:
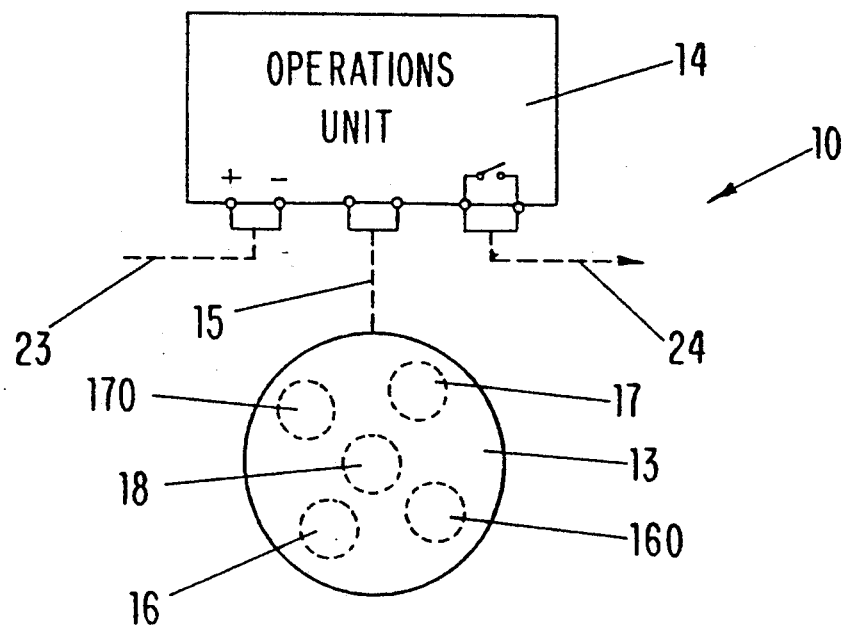
FIG. 3 is a block diagram showing the inventive apparatus, which comprises an operations unit and a detector unit that is connected therewith.

Referring now to the drawing in detail, the apparatus 10 essentially comprises a detector unit 13 and an operations unit 14, which are interconnected via a connecting line 15 in the form of a two-wire or other multi-wire line (see FIG. 3). The detector unit 13 is powered externally via a supply voltage 23. The evaluation of the detection results of the electrodes 16, 17 and the sensor means 18 of the detector unit 13 is carried out in the operations unit 14, and in particular in conformity with generally known electronic principles, so that the same do not require further discussion at this point. Also provided in the operations unit 14 is an alarm unit that serves to provide an electrical and/or audible signal that a liquid 12 has been detected. It would also be possible to connect the alarm unit via an electrical line 24 to a central control means for alarm lines or to an evaluation computer; this is particularly expedient where a large building is being monitored.

The detector unit 13 comprises a housing 130 that can be closed off by a cover means that can be removed; in the illustrated embodiment, the housing 130 has a cylindrical cross-sectional configuration. The housing 130 is preferably made of plastic, so that no separate insulating measures have to be provided for accommodating the electrodes 16, 17 in the base 131 of the housing; this also applies for the accommodation of the sensor means 18 in the base 131. Also provided in the housing 130 is a printed circuit board that serves for accommodating non-illustrated electronic components and for receiving the cable connections between the electrodes 16, 17 and the sensor means 18, with the electrical line 15 to the operations unit 14 also being connected to the printed circuit board. The electrical circuitry provided on the printed circuit board 132 is provided in conformity with generally known electronic principles, so that any further discussion thereof at this point is not required.

As can be seen from the dashed-line illustration in FIG. 3 of the electrodes 16, 17 and 160, 170, a total of four electrodes are provided in the base 131 of the detector unit 13. However, it is to be understood that this illustrates merely one exemplary embodiment, since it is possible in principle, starting with a minimum provision of the apparatus 10 with one electrode pair 16, 17, to provide any number of electrode pairs, depending upon the application for which the apparatus is intended. The electrodes 16, 17 can be embodied as integral turned parts and can be either fixedly disposed in the housing 130, or the electrodes 16, 17 could also be embodied in such a way that they are screwed or otherwise secured in the housing 130 as complete units, with any number of suitable means for fastening electrode pairs in the base 131 of the detector unit 13 being conceivable, so that if necessary the number of necessary electrode pairs 16, 17 can be varied.

It can also be expedient to universally provide the electrode 16, 17 in the housing 130, and to merely provide different lengths for the projections 20, which have a given length 21 and extend from the electrode surface 19, which is parallel to the surface 11 upon which the apparatus 10 rests. By providing different lengths of projections 20, the requirements of a particular application can be met, for example use of the apparatus 10 on an absolutely smooth or flat surface 11 (e.g. the floor of a plant or arena), or on a surface 11 that is in the form of a textile floor covering. Such a floor covering having a varying pile height can be taken account of (as seen in FIG. 2a) by varying the length 21 of the projections 20, i.e. by using longer or shorter projections as appropriate.

Figure 2:
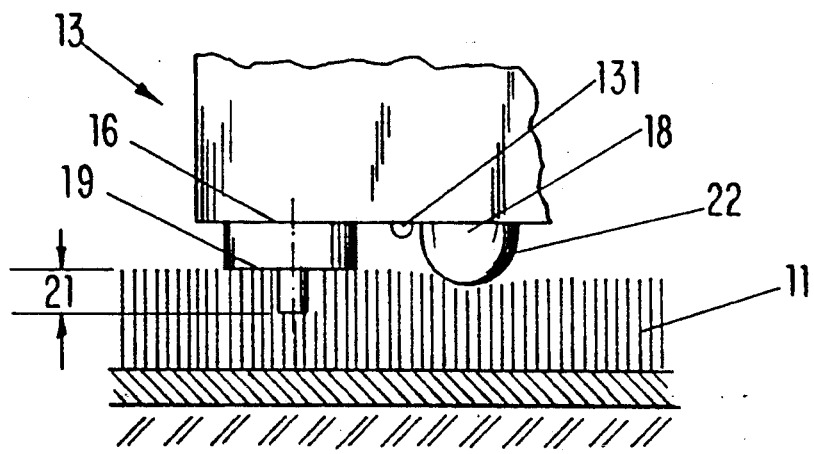
FIG. 2 shows a portion of the detector unit, the electrodes and the light-sensitive surface of the sensor means of which rest upon, or extend partially into, a level textile floor covering.
Figure 2A:
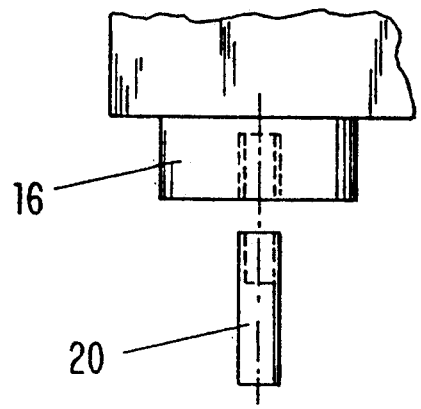
FIG. 2a illustrates threadably attachable projections for use with the detector unit of FIGS. 1 and 2.

As can be seen from FIG. 2, the electrode 16 can easily extend into a textile floor covering, and in particular to such a depth that the preferably circular electrode surface 19 can reliably come to rest upon the upper surface of the pile of the textile floor covering.

Disposed between the electrodes 16, 17 and/or 160, 170 is the sensor means 18, the optically active surface 22 of which is directed toward the surface 11 upon which the apparatus 10 is positioned. When the inventive apparatus is positioned on a smooth, solid surface 11 as illustrated in FIG. 1, the length 21 of the projections 20 is such that the optically active surface 22 of the sensor means 18 does not contact the surface 11. This ensures a certain mechanical protection of the sensor means 18.

In the illustration of FIG. 2, the electrodes 16, as well as the other non-illustrated electrodes of the electrode pairs, ensure that an adequate space is provided between the underside of the base 131 and the surface formed by the upper side of the carpet pile of a textile floor covering, so that liquid can enter beneath the underside of the housing 130 and can moisten or wet the optically active surface 22 of the sensor means 18. In this connection, the height of the electrodes is selected in such a way that when the detector unit 13 rests upon a textile floor covering, the optical sensor means 18 can extend slightly into the textile structure or pile, for example to a depth of 1 mm. In this way, already a liquid level of Since the projections 20 extend into the textile structure, electrically conductive liquids 12 are already detected even before a soaked floor covering has reached a visible liquid level.

As indicated previously, the supply and signal current is guided through a two-wire or multi-wire electrical line between the detector unit 13 and the operations unit 14. If the connection is reversed, a built-in semiconductor or crystal diode or rectifier effects a significant change in current and hence triggers an alarm signal. This ensures that even an unskilled person can make the apparatus 10 operational. In addition, if the supply voltage is low voltage, any danger to persons or objects is precluded.

The present invention is, of course, in no way restricted to the specific disclosure of the specification and drawing, but also encompasses any modifications within the scope of the appended claims.

What is claimed is:

1. An apparatus for detecting and reporting the presence of liquid on a surface, comprising:
    a detector unit that rests on said surface, with said detector unit including at least one pair of spaced-apart electrodes for conductively detecting said liquid, with said detector unit resting on said surface via said electrodes, and with said detector unit further including a sensor means that is directed toward said surface and serves for optically detecting said liquid; and
    an operations unit, with said detector unit and said operations unit being electrically interconnected.

2. An apparatus according to claim 1, in which each of said electrodes includes a surface means that extends essentially parallel to said surface, with a pin-like projection being provided that extends from said electrode surface means.

3. An apparatus according to claim 2, in which said projection is integral with said electrode.

4. An apparatus according to claim 2, which includes variable length projections.

5. An apparatus according to claim 2, in which said projection is detachably connected to said electrode.

6. An apparatus according to claim 2, in which the length of said projection is such that when said apparatus rests upon a solid surface, at least an optically active surface of said sensor means does not contact said surface.

7. An apparatus according to claim in which at least an optically active surface of said sensor means is disposed between said electrodes.

8. An apparatus according to claim 1, in which the electrical current consumption of said detector unit, which changes when said liquid is detected, provides a measurement parameter for the production of at least one of an electrical and audible signal by said apparatus.

9. An apparatus according to claim 1, in which said operations unit includes means for evaluating the detection results of said electrodes.

* * * * *